US012690991B2

(12) United States Patent
Chandra et al.

(10) Patent No.: US 12,690,991 B2
(45) Date of Patent: Jul. 28, 2026

(54) INCREASED DRAINAGE AND DECREASED INTERNAL STRESS URETERAL STENT DESIGN

(71) Applicant: Cook Medical Technologies LLC, Bloomington, IN (US)

(72) Inventors: Santanu Chandra, West Lafayette, IN (US); Richard Swift, South Bend, IN (US); Conor Heffernan, Limerick (IE); Nathan Killey, Appleton, WI (US); Jonathan Sheets, Greenwood, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 121 days.

(21) Appl. No.: 17/494,008

(22) Filed: Oct. 5, 2021

(65) Prior Publication Data

US 2022/0110772 A1 Apr. 14, 2022

Related U.S. Application Data

(60) Provisional application No. 63/089,149, filed on Oct. 8, 2020.

(51) Int. Cl.
*A61F 2/04* (2013.01)
*A61F 2/88* (2006.01)
(Continued)

(52) U.S. Cl.
CPC ................. *A61F 2/88* (2013.01); *A61F 2/04* (2013.01); *A61M 27/008* (2013.01); *A61F 2002/048* (2013.01)

(58) Field of Classification Search
CPC ...... A61F 2230/0023; A61F 2230/0024; A61F 2/04; A61F 2002/048; A61F 2230/0091;
(Continued)

(56) References Cited

U.S. PATENT DOCUMENTS 4,820,262 A * 4/1989 Finney ................ A61M 27/008
604/8
5,599,291 A * 2/1997 Balbierz ................ A61L 31/10
604/8
(Continued)

FOREIGN PATENT DOCUMENTS

CN 107 510 878 A 12/2017
CN 208 065 305 U 11/2018
(Continued)

OTHER PUBLICATIONS

Extended European Search Report in Corresponding European Application No. 21201784.2, dated Mar. 25, 2022 (9 pages).
(Continued)

*Primary Examiner* — David H Willse
(74) *Attorney, Agent, or Firm* — MacMillan, Sobanski & Todd, LLC

(57) ABSTRACT

A ureteral stent may comprise an elongate member with an internal-luminal space. The member may have at least one end coiled in a pigtail-shape, a substantially straight portion, and a plurality of side ports wherein the plurality of side ports are located only in the substantially straight portion and are disposed along a spiral or helix where each side port is located radially and longitudinally offset relative to each adjacent side port.

18 Claims, 6 Drawing Sheets

(51) Int. Cl.
    *A61F 2/94*         (2013.01)
    *A61M 27/00*      (2006.01)

(58) Field of Classification Search
    CPC ...... A61F 2250/0023; A61F 2250/0024; A61F
             2002/047; A61F 2/88; A61F 2250/0013;
             A61F 2250/0014; A61M 25/0017; A61M
             27/008; A61M 27/002; A61M 27/0017;
                  A61M 25/007; A61M 25/0015
    See application file for complete search history.

(56) References Cited

U.S. PATENT DOCUMENTS

| | | | |
|---|---|---|---|
| 6,719,804 B2 | 4/2004 | St. Pierre | |
| 7,682,401 B2 | 3/2010 | Deal | |
| 8,048,168 B2 | 11/2011 | Dillinger | |
| 8,048,171 B2 * | 11/2011 | Li | A61M 27/002 |
| | | | 604/8 |
| 8,657,884 B2 | 2/2014 | Smouse | |
| 9,333,063 B2 | 5/2016 | Li et al. | |
| 9,694,110 B2 | 7/2017 | Sheth | |
| 9,937,067 B2 * | 4/2018 | Pendleton | A61F 2/852 |
| 10,080,641 B2 | 9/2018 | Tang et al. | |
| 10,201,441 B2 | 2/2019 | Gellman | |
| 10,258,485 B2 | 4/2019 | Davoudi et al. | |
| 2002/0188246 A1 | 12/2002 | Hayner et al. | |

| | | | |
|---|---|---|---|
| 2004/0181186 A1 * | 9/2004 | Gellman | A61M 27/008 |
| | | | 623/23.71 |
| 2007/0225679 A1 * | 9/2007 | Deal | A61F 2/82 |
| | | | 604/524 |
| 2007/0298069 A1 | 12/2007 | Bucay-Couto et al. | |
| 2008/0234659 A1 | 9/2008 | Cheng et al. | |
| 2009/0187254 A1 | 7/2009 | Deal et al. | |
| 2011/0098631 A1 | 4/2011 | McIntyre et al. | |
| 2012/0095566 A1 * | 4/2012 | Teague | A61F 2/04 |
| | | | 623/23.7 |
| 2012/0179144 A1 * | 7/2012 | Carleo | A61M 25/0017 |
| | | | 604/544 |
| 2013/0231752 A1 | 9/2013 | Rosenbaum et al. | |
| 2014/0052272 A1 * | 2/2014 | Amos, Jr. | A61M 27/008 |
| | | | 623/23.69 |
| 2016/0199170 A1 | 7/2016 | Biltz | |
| 2017/0348512 A1 * | 12/2017 | Orr | A61M 1/73 |
| 2019/0105474 A1 | 4/2019 | Sheibley | |

FOREIGN PATENT DOCUMENTS

| | | | |
|---|---|---|---|
| CN | 211 096 882 | 7/2020 | |
| WO | WO 2016/131938 A1 * | 8/2016 | A61M 25/04 |

OTHER PUBLICATIONS

European Communication pursuant to Article 94(3) EPC, Application No. 21201784.2, dated Jul. 25, 2024.

* cited by examiner

--Prior Art--

INCREASED DRAINAGE AND DECREASED INTERNAL STRESS URETERAL STENT DESIGN

CROSS-REFERENCE TO RELATED APPLICATIONS

This application is a non-provisional application which claims priority to U.S. provisional application Ser. No. 63/089,149, filed Oct. 8, 2020, which is incorporated by reference herein in its entirety.

TECHNICAL FIELD

Embodiments disclosed herein generally relate to stents, and more particularly to stents configured for use in and through a ureter.

BACKGROUND

Ureteral stents are widely used prior to and/or after various urological procedures and serve to provide drainage of urine from the kidney into the bladder with an indwell time of up to 12 months. Typically, ureteral stents comprise an elongate member with an internal-luminal space, the member having at least one end coiled in a pigtail-shape, a substantially straight portion, and a plurality of side ports. While the stent is indwelling, urine passes through the internal-luminal space between the ureter and the ureteral stent as well as passing into and out of side ports located along the length of the stent, which allows urine to flow through the stent inner lumen. The size, shape, and location of the side ports dictate the drainage characteristics of the stent. Larger side port diameter and a greater number of side ports may lead to more removal of material that increases the drainage characteristics but may lead to high stress in the device. If the stress is allowed to reach a high enough level, the device may fail, resulting in a delayed procedure, fragmenting of the stent, and the potential for additional intervention. Also, not all the side ports are uniformly active when deployed in the ureter, which leads to stasis regions inside the inactive side ports. These stasis regions may lead to encrustation formations. Therefore, strategic placement of the side ports is crucial in optimization of the flow characteristics and mitigating the risk of encrustations. Furthermore, devices with strategic placement of the side ports may offer reduced manufacturing complexity and cost.

The stent of the current disclosure may rectify the formation of encrustation at side ports locations due to improper drainage characteristics. One objective of the present disclosure is to improve the drainage characteristics by strategic placement of the side ports in the kidney-ureter junction as well as to reduce the internal stress present within the stent during use. The strategic placement includes identification of the high drainage location in a stent after its placement in the human physiology and then increasing the number of side ports in that location of the kidney-ureter and ureter-bladder junctions and reducing the number of side ports in low drainage locations inside the kidney, bladder and ureter.

BRIEF SUMMARY

The disclosed invention relates generally to a medical device assembly, more specifically to a ureteral stent.

One general aspect of the present disclosure includes a stent comprising an elongate member, the elongate member having a first coil section defining a lumen and comprising a first coil, a first substantially straight section defining a lumen, a second substantially straight section defining a lumen and located between the first coil section and the first substantially straight section, and a plurality of side ports wherein the plurality of side ports are located only in the substantially straight sections.

Other systems, methods, features and advantages of the invention will be, or will become, apparent to one with skill in the art upon examination of the following figures and detailed description. It is intended that all such additional systems, methods, features, and advantages be within the scope of the invention, and be encompassed by the following claims.

BRIEF DESCRIPTION OF DRAWINGS

The present disclosure can be better understood with reference to the following drawings and description. The components in the figures are not necessarily to scale, emphasis instead being placed upon illustrating the principles of the present disclosure. Moreover, in the figures, like-referenced numerals designate corresponding parts throughout the different views.

DETAILED DESCRIPTION

Figures 1, 1A:
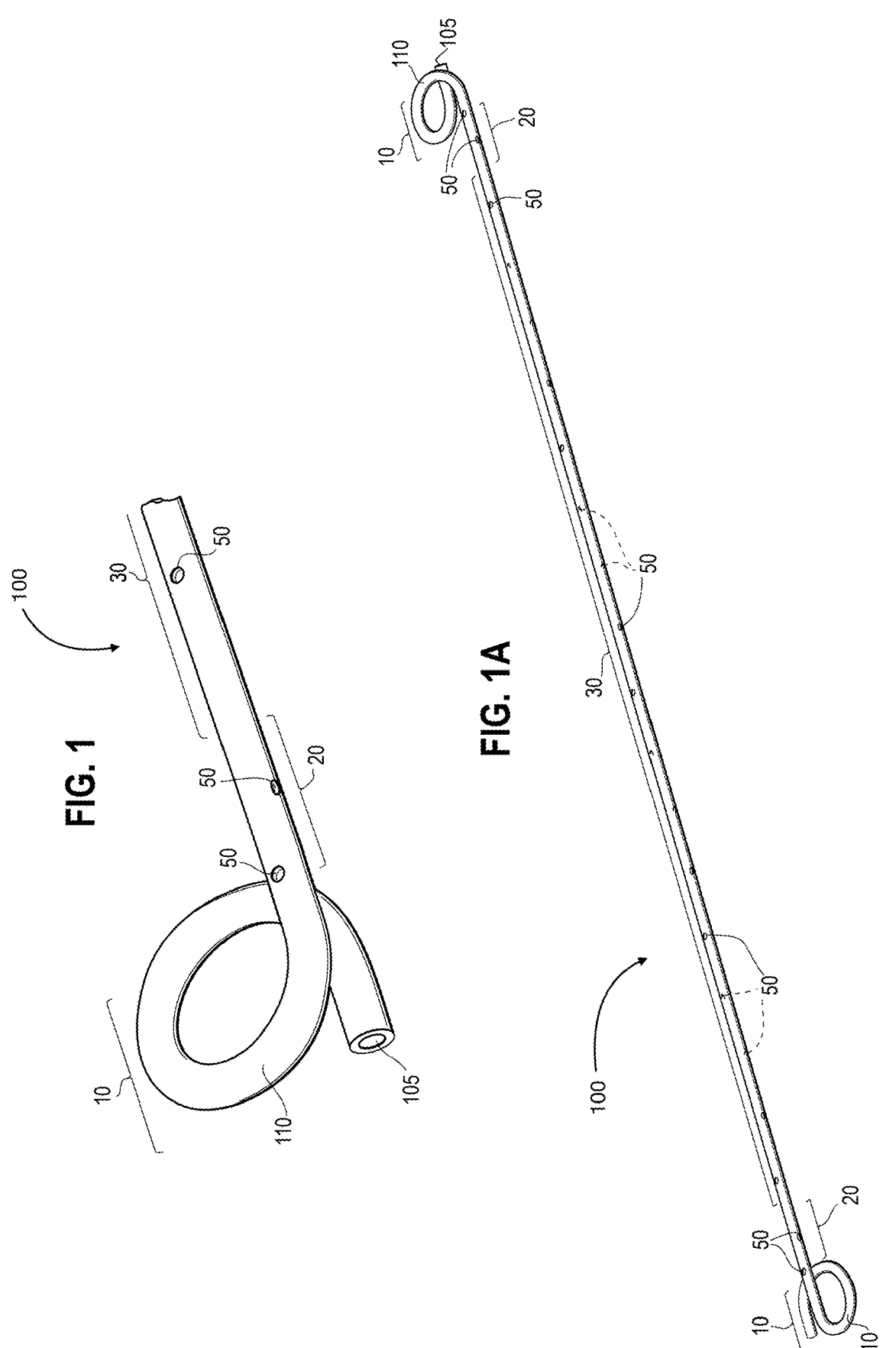
FIG. 1 is an illustration showing a perspective view of one end portion of a stent in accordance with certain aspects of the present disclosure.
FIG. 1A is an illustration showing a perspective view of a stent in accordance with certain aspects of the present disclosure (e.g., FIG. 1), and indicating also that the side on which end curls/coils lie can go the same direction or opposite directions in different embodiments.

Various aspects are described below with reference to the drawings in which like elements generally are identified by like numerals. The relationship and functioning of the various elements of the aspects may better be understood by reference to the following detailed description. However, aspects are not limited to those illustrated in the drawings or explicitly described below. It also should be understood that the drawings are not necessarily to scale, and in certain instances details may have been omitted that are not necessary for an understanding of aspects disclosed herein, such as conventional material, construction, and assembly. The terms "about," "substantially," "generally," and other terms of degree, when used with reference to any volume, dimension, proportion, or other quantitative or qualitative value, are intended to communicate a definite and identifiable value within the standard parameters that would be understood by one of skill in the art (equivalent to a medical device engineer with experience in this field), and should be interpreted to include at least any legal equivalents, minor but functionally-insignificant variants, standard manufacturing tolerances, and including at least mathematically significant figures (although not required to be as broad as the largest range thereof). For example, the term "substantially straight" means at least more nearly straight than curved, but generally and preferably means as nearly straight as possible within realistic physical constraints of the materials used and manufacturing tolerances therefor.

Figure 2:
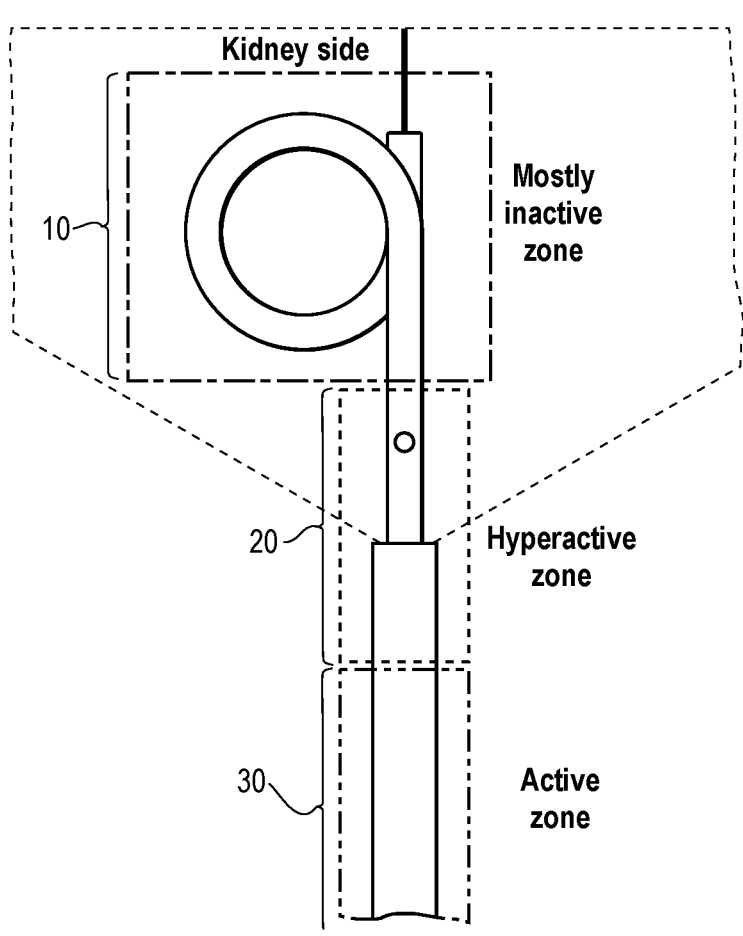
FIG. 2 is an illustration showing relative positions of the device elements within a human body.

Referring to FIGS. 1-1 A, a pigtail stent 100 may include an elongate tubular member 110 with an internal-luminal space 105, the member 110 having at least one pigtail curl 10 (alternatively called a coil, as it forms a nearly helical loop) at an end, a substantially straight 20 portion near the beginning of the pigtail curl, a substantially straight portion of the stent body 30, and a plurality of side ports 50. Substantially straight portions 20, 30 refer to portions of the stent 100 that establishes a substantially straight profile in a nominal direction, which need not be perfectly linear. Because stent 100 is generally made of a flexible material, the substantially straight portions 20, 30 may follow an arcuate lumen deployed therein. As should be understood with reference to FIG. 1A, the stent 100 may actually be generally symmetrical in gross construction (e.g., double pigtailed) and/or in fine detail (e.g., number and placement of side ports), where a double-pigtail embodiment may have the first and second coils at opposite ends matching or mirroring each other along or across any axis of the device and including a second coiled portion 10 and third substantially straight portion 20, at the opposite end of the second first substantially straight portion 30. FIG. 2 illustrates relative positions of the curl 10, the second substantially straight portion 20 near the beginning of the curl 10, and the substantially straight portion of the body 30 inside a human body. When disposed in a human body, the first pigtail curl 10 may be located inside kidney whereas the substantially straight portions 20, 30 may generally be located in/through a ureter, and a second pigtail curl 10 (if present) may be located in the bladder of the body where the device is installed. Typical stent dimensions may be between 5 Fr-9 Fr (about 1.66 to about 3 mm in diameter) and about 15 to about 35 cm in length including one or two coiled pigtails (meaning that the uncoiled length would be greater).

In one embodiment, the stent 100 may have a plurality of side ports 50 only on substantially straight portions 20, 30, with no side ports along/around the coil 10 of the pigtail. Specifically, side ports 50 on the substantially straight portion near the beginning of the pigtail curl 10 may be spaced 0.5 cm apart, with adjacent side ports 50 lying along an axis that is rotated/offset 90° from the other side ports 50 along the body of the substantially straight portion. The number of side ports 50 in the substantially straight portion 20 near the beginning of the pigtail curl 10 determines the drainage. For example, increasing the number of side ports 50 in the substantially straight portion 20 near the beginning of the pigtail curl 10 may result in greater drainage with the same flow rate through the lumen within which the stent is deployed, such as the ureter. Thus, the number of side ports 50 in the substantially straight portion near the beginning of the pigtail curl 10 may vary depending on the desired drainage characteristics. In one embodiment, the number of side ports 50 in the substantially straight portion 20 near the beginning of the pigtail curl 10 may be five, while in other embodiments it may be alternative numbers, such as 3-10 ports, inclusive of all numbers within this range. Additionally, side ports 50 in the substantially straight portion of the body 30 may be spaced apart at various longitudinal distances. For example, side ports 50 in the substantially straight portion of the body 30 may be longitudinally spaced at least up to 5 mm or 1 cm apart from each other, or further apart. The side ports 50 may be, but do not need to be, uniformly spaced longitudinally apart from each other. For example, the side ports 50 may be longitudinally spaced about 5 mm from each other along the substantially straight portion 20, and then spaced further apart along the middle substantially straight portion 30. For another example, side ports 50 in the substantially straight portion of the body 30 may be spaced 3 cm apart from each other. The side ports 50 in the substantially straight portion of the body 30 may be positioned upon the portion such that the side ports are positioned at/offset by 90° angles between adjacent, longitudinally separated side ports along the length of the substantially straight portion. In other embodiments, there may be different angles between adjacent side ports, such as 30, 45, 60, or 75 degrees. Stated differently, each of the plurality of side ports on the second substantially straight section is offset rotated (e.g., 90° or some other amount of about 30°-90°) relative to each adjacent side port, such that they are disposed along a spiral or helix where each side port is located radially and longitudinally offset relative to each longitudinally-adjacent side port.

Figure 3A:
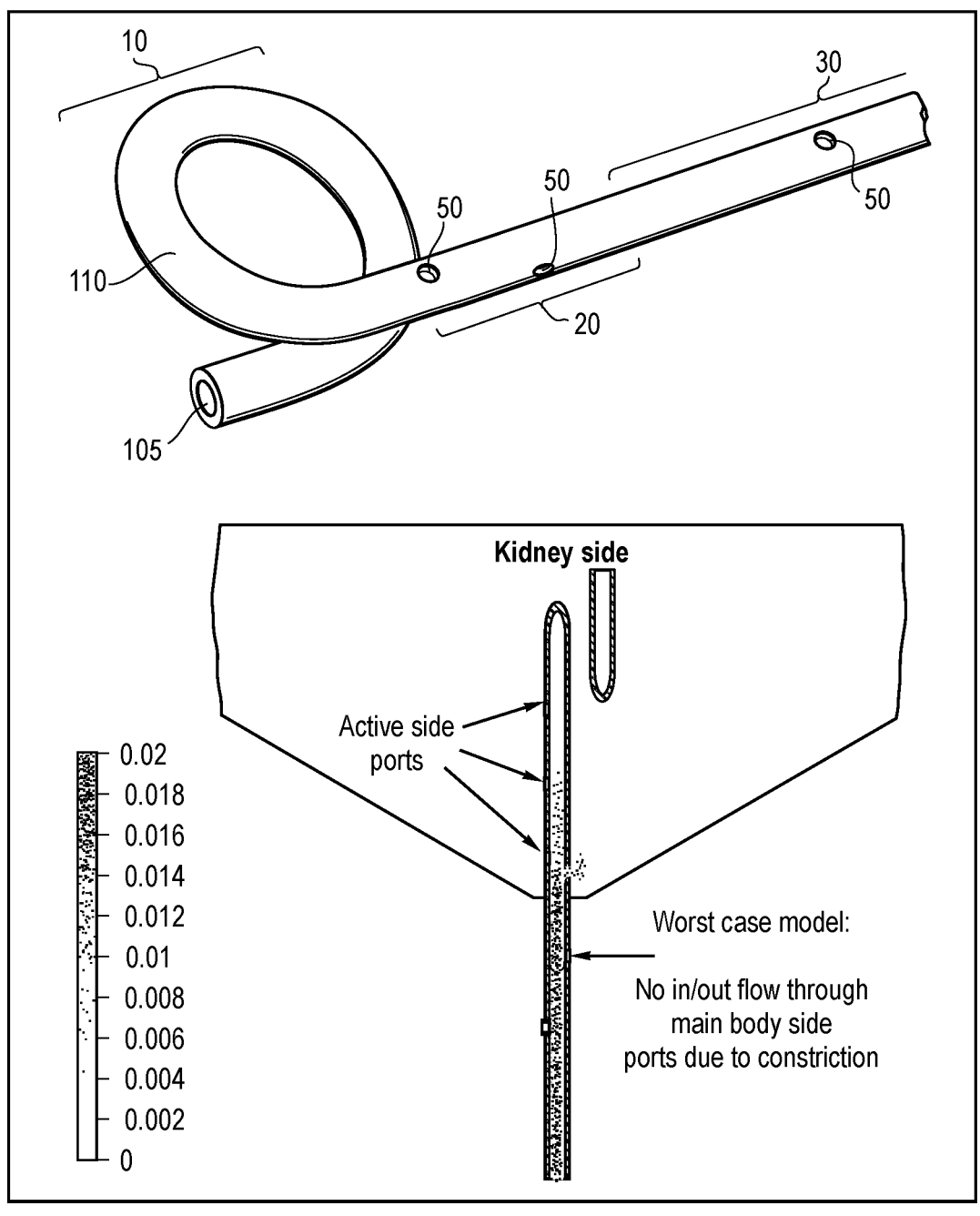
FIGS. 3A-B show a comparison of flow characteristics, with FIG. 3B showing flow characteristics of a pigtail stent having side ports in pigtail curl and FIG. 3A showing flow characteristics of a pigtail stent in accordance with certain aspects of the present disclosure.
Figure 3B:
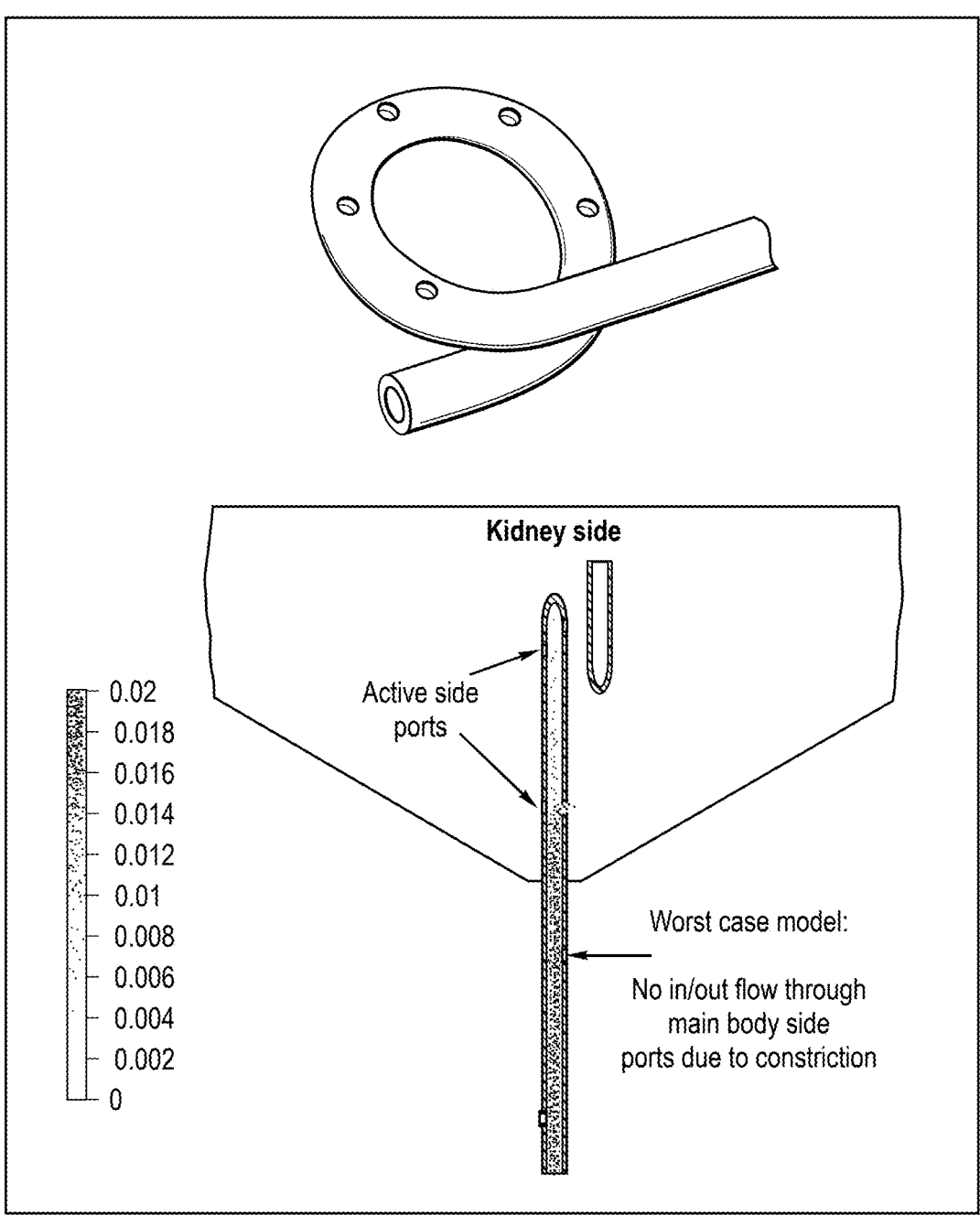

The drainage along the substantially straight portions 20, 30 of the stent can be characterized by calculations of the flow resistance, which is a ratio of pressure gradient and flow rate at inlet. The pressure gradient is defined as the pressure difference between inlet and outlet. Not every one of the side ports is uniformly active when deployed in the ureter. However, proper drainage characteristics are important because stasis regions, which may be formed inside inactive side ports, may lead to encrustation formations. Referring to FIGS. 3A-3B, a device constructed in accordance with certain aspects of the present disclosure (e.g., as shown in FIG. 1 and the upper portion of FIG. 3A) exhibited a reduced flow resistance of the device by 10% for a flow rate of 1 mL/min compared to a device having side ports along the coiled pigtail portion (as shown in the upper portion of FIG. 3B). Specifically, FIG. 3B shows a colorimetric diagram with flow characteristics of a device having side ports along the coiled pigtail portion. The device having side ports along the pigtail portion exhibit a substantial decrease in drainage inside kidney through most of the side ports in the pigtail region. One side port around the junction of kidney and bladder region, which is equivalent to the substantially straight portion near the beginning of pigtail curl, is hyperactive. Therefore, FIG. 3B flow diagram shows two active side ports as in a prior art catheter. On the other hand, FIG. 3A shows a colorimetric diagram with flow characteristics of the device in accordance with certain aspects of the present disclosure having more side ports around the junction of kidney and bladder region but having no side ports along the coiled pigtail portion. A device constructed in accordance with certain aspects of the present disclosure exhibits gradual increase in drainage in the kidney-ureter junction region, and thus has more side ports that are relatively active as compared to prior art stents that have side ports along the coiled pigtail. FIG. 3A shows three active side ports. Eliminating the side ports on the pigtail curl and increasing the number of side ports on the substantially straight portion near the beginning of pigtail curl in accordance with certain aspects of the present disclosure reduces the number of stasis locations inside the inactive side ports, thereby reducing the risk for encrustation.

Figure 4A:
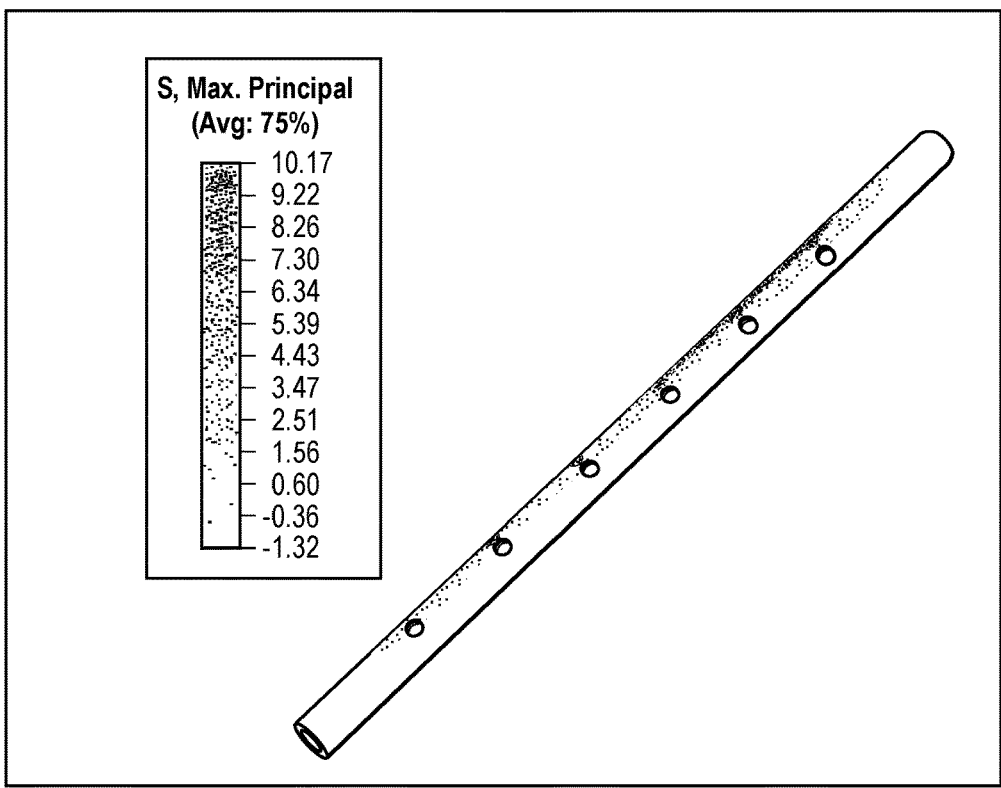
FIGS. 4A-4B show a comparison of ureteral stent stress levels after pigtail unwinding, with FIG. 4A showing stress level of a pigtail stent having side ports along the coil of the pigtail section and FIG. 4B showing stress level of a pigtail stent in accordance with certain aspects of the present disclosure like the embodiments of FIGS. 1-1A.
Figure 4B:
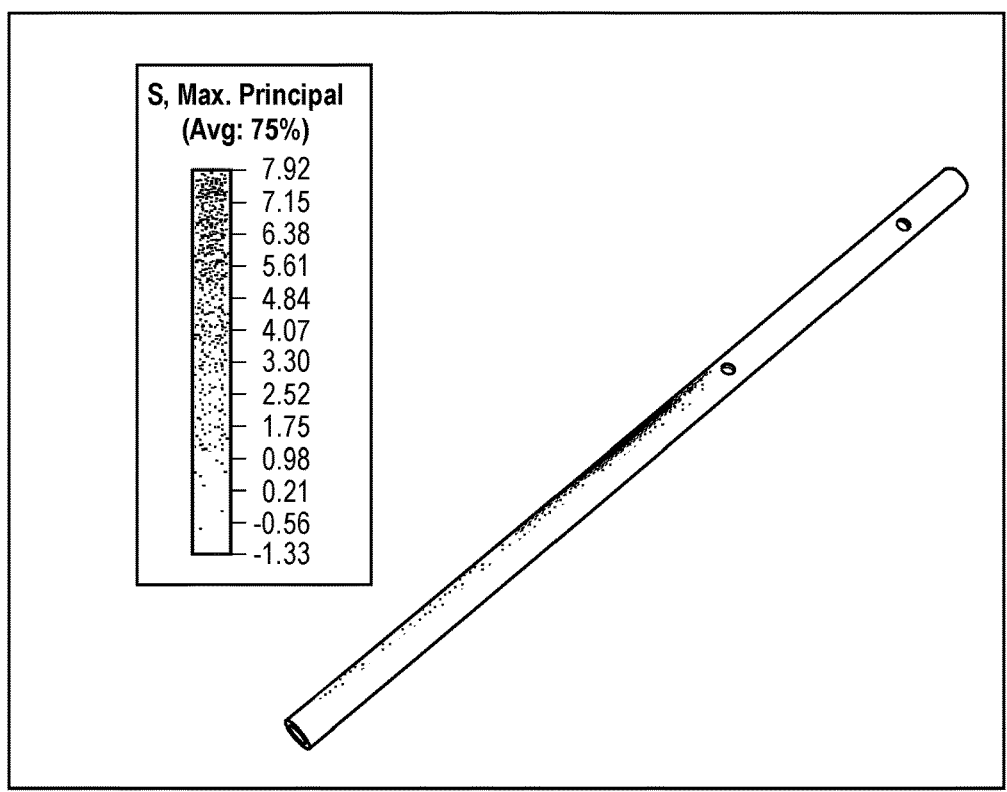

Referring to FIGS. 4A-4B, the device in accordance with certain aspects of the present disclosure exhibited a decreased stress level during the straightening of the pigtail curl 10, which is identified as one of the highest stress scenarios experienced by a stent during use. FIG. 4A shows a colorimetric representation of stress levels of the straightened pigtail portion of a device having side ports linearly along the pigtail curl whereas FIG. 4B shows stress levels of the straightened pigtail portion of the device having no side ports along the pigtail portion in accordance with certain aspects of the present disclosure. Stress levels along the straightened portion of the device constructed in accordance with certain aspects of the present disclosure were generally lower than that of the device having side ports along the pigtail portion (e.g., as shown in the upper portion of FIG. 3A). Particularly, the decrease in stress level was of 28% compared to that of the pigtail stent having side ports on the coiled pigtail portion. This presents advantages for the device that will readily be appreciated by those of skill in the art, including with regard to maintaining device integrity and/or to minimizing stresses applied to patient tissues during installation and removal of a stent constructed in keeping with this disclosure.

Figure 5A:
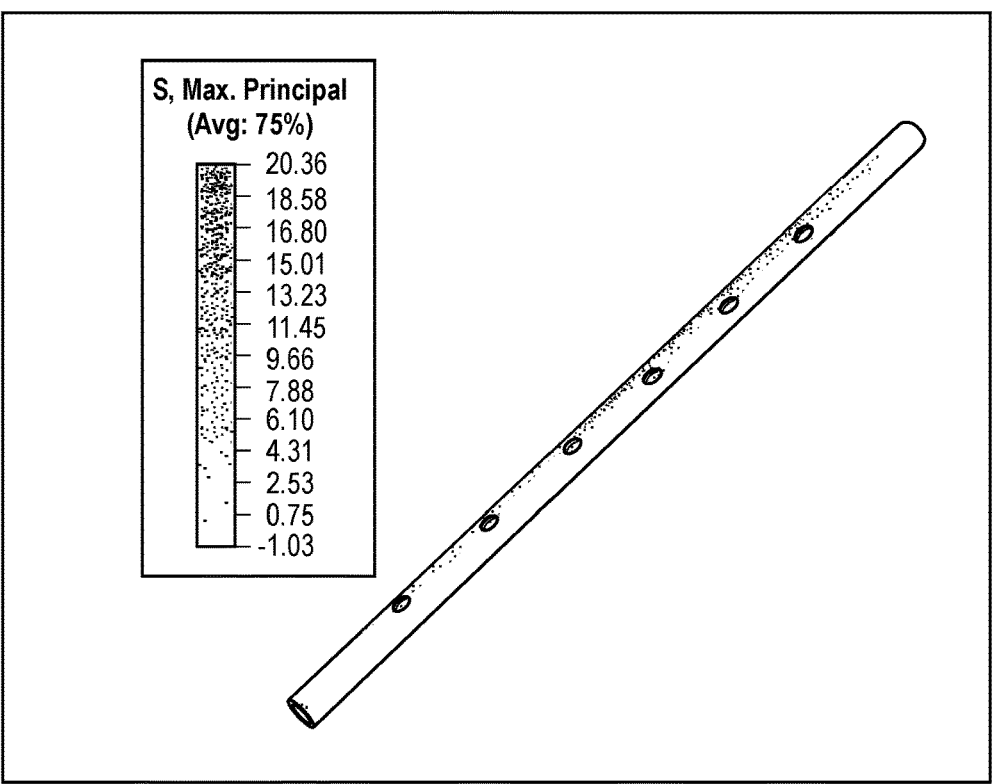
FIGS. 5A-5B show a comparison of ureteral stent stress levels after pigtail unwinding and extraction force application, FIG. 5A showing stress level of a pigtail stent having side ports on pigtail section and FIG. 5B showing stress level of a pigtail stent in accordance with certain aspects of the present disclosure.
Figure 5B:
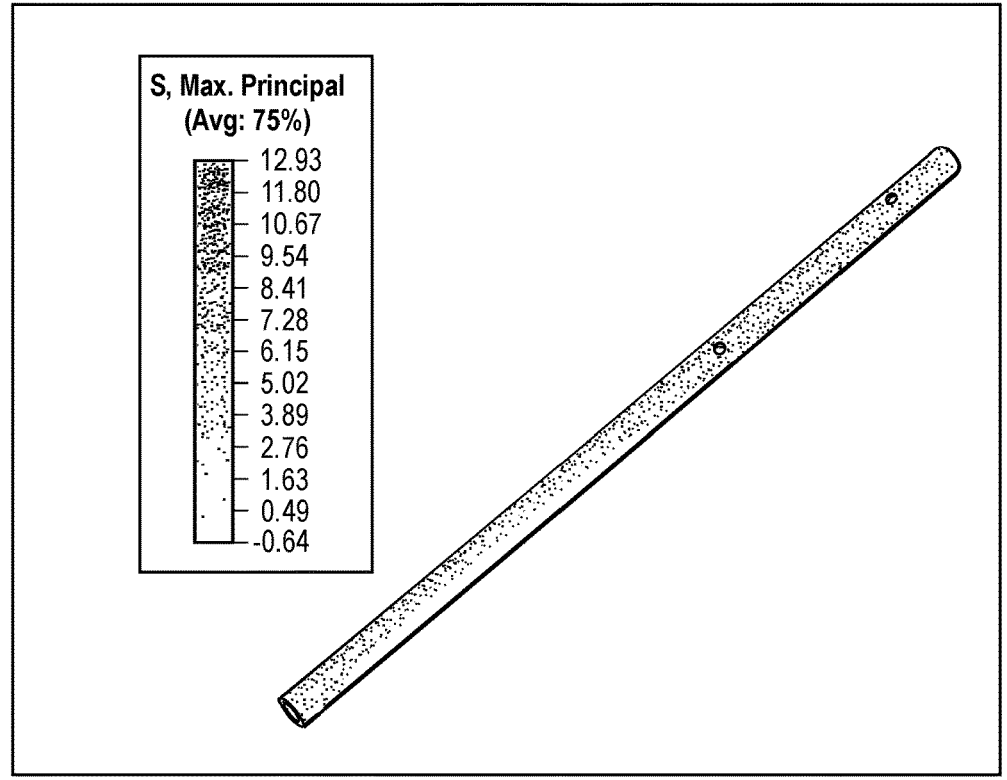

Referring to FIGS. 5A-5B, the device in accordance with certain aspects of the present disclosure exhibited a decreased peak stress during exaggerated tensile extension of the stent, which reflects the worst-case expected loading scenario during stent retrieval, when the coiled pigtail portion may be forced out of its coil to be substantially or absolutely straight. Specifically, FIG. 5A shows a colorimetric diagram of the stress level of a device having side ports linearly along the pigtail portion (e.g., as shown in the upper portion of FIG. 3A), whereas FIG. 5B shows a colorimetric diagram of the stress level of the device having no side ports along the pigtail portion in accordance with the present disclosure (e.g., as shown in FIG. 1). Stress levels of the straightened portion of the device in accordance with certain aspects of the present disclosure were markedly lower than that of the device having side ports along the coiled pigtail portion. Specifically, the decrease was 57% compared to that of the pigtail stent having side ports on the pigtail portion.

In addition to improved performance characteristics, devices without side ports in the curled pigtail region in accordance with certain aspects of the present disclosure offer generally reduced manufacturing complexity and cost. Those factors—along with the above-described changes in stresses during device life and usage, and in improved flow with corresponding reduced risk of encrustation that would diminish device efficacy—demonstrate the criticality of the present inventive features.

While the preferred embodiments of the disclosure have been described, it should be understood that the disclosure is not so limited and modifications may be made without departing from the scope of the present disclosure. The scope of the invention is defined by the appended claims, and all devices that come within the meaning of the claims, either literally or by equivalence, are intended to be embraced therein.

We claim:

1. A stent comprising:
an elongate member comprising a monolithic body defining a single lumen and comprising:
a first coil section defining a coil section lumen and comprising a first substantially helical coil;

a first substantially straight section defining a first substantially straight section lumen continuous with the coil section lumen, the first substantially straight section extending from the first substantially helical coil and having a first length;
a second substantially straight section defining a second substantially straight section lumen continuous with the first substantially straight section lumen, the second substantially straight section extending from the first substantially straight section and having a second length longer than the first length; and
a plurality of side ports in each of the first and second substantially straight sections, wherein a first density of the plurality of side ports in the first substantially straight section is greater than a second density of the plurality of side ports in the second substantially straight section;
wherein each of the plurality of side ports on the second substantially straight section is offset rotated from about 30° to about 90° relative to each adjacent side port;
wherein each of the plurality of side ports is located only on the substantially straight sections; and
wherein the single lumen comprises the coil section lumen, the first substantially straight section lumen, and the second substantially straight section lumen.

2. The stent of claim 1, wherein the plurality of side ports on the first substantially straight section includes three to ten side ports.

3. The stent of claim 1, wherein each of the plurality of side ports on the first substantially straight section is longitudinally spaced 5 mm apart from each other.

4. The stent of claim 1, wherein each of the plurality of side ports on the second substantially straight section is offset rotated 90° relative to each adjacent side port.

5. The stent of claim 1, wherein each of the plurality of side ports on the second substantially straight section is spaced 3 cm longitudinally apart from adjacent side port(s).

6. The stent of claim 1, wherein the elongate member further comprises:
a second coil section defining a lumen and comprising a second substantially helical coil; and
a third substantially straight section defining a lumen and located between the second substantially straight section and the second coil section.

7. The stent of claim 6, further comprising a plurality of side ports in the third substantially straight section;
wherein each of the plurality of side ports on the third substantially straight section is spaced 5 mm longitudinally apart from adjacent side port(s).

8. The stent of claim 1, wherein the plurality of side ports in the first substantially straight section have more drainage activity than the plurality of side ports in the second substantially straight section.

9. The stent of claim 8, wherein no side ports are disposed along the first substantially helical coil.

10. The stent of claim 1, wherein no side ports are disposed along the first substantially helical coil.

11. A stent comprising:
an elongate tubular member comprising a monolithic body defining a single lumen and comprising:
a first coil section defining a first coil section lumen and comprising a first coil;
a second coil section defining a second coil section lumen and comprising a second coil;
a first substantially straight section defining a first substantially straight section lumen continuous with the first coil section lumen, the first substantially straight section extending from the first coil section and configured for placement in a kidney-ureter junction of a patient;

a second substantially straight section extending from the first substantially straight section and defining a second substantially straight section lumen continuous with the first substantially straight section lumen;

a third substantially straight section located between the second coil section and the second substantially straight section and configured for placement in a ureter-bladder junction of the patient;

a plurality of active side ports in the first substantially straight section;

a plurality of side ports in the second and third substantially straight sections, wherein the plurality of side ports in the second substantially straight section have less drainage activity than the plurality of active side ports in the first substantially straight section, the plurality of side ports located on the second and third substantially straight sections;

wherein each of the plurality of side ports along the second substantially straight section is offset rotated from about 30° to about 90° relative to each adjacent side port;

wherein the plurality of active side ports in the first substantially straight section are configured to provide increased drainage activity in the kidney-ureter junction of the patient;

wherein the first and third substantially straight sections are shorter than the second substantially straight section; and wherein the single lumen extends continuously through the first coil section, the first, second, and third substantially straight sections, and the second coil section, as well as also communicating with an exterior of the elongate tubular member through the side ports.

12. The stent of claim 11, wherein at least some of the plurality of side ports are uniformly spaced away from each other.

13. The stent of claim 11, wherein the plurality of side ports along the first substantially straight section includes three to ten side ports.

14. The stent of claim 11, wherein at least some of the plurality of side ports are spaced away from each other by about 5 mm to about 3 cm.

15. The stent of claim 11, wherein at least some of the plurality of side ports are more closely spaced away from each other along the first and third substantially straight sections than along the second substantially straight section.

16. The stent of claim 11, wherein no side ports are disposed along the first coil.

17. The stent of claim 16, wherein no side ports are disposed along the second coil.

18. A ureteral stent comprising:

an elongate tubular member comprising a monolithic body defining a single lumen and comprising:

a first coil configured for placement in a kidney of a patient;

a first section extending from the coil and configured for placement in a kidney-ureter junction of the patient;

a second section extending from the first section having a length longer than the first section and configured for placement in the ureter of the patient;

a first plurality of active side ports in the first section, each side port of the first plurality of side ports in communication with the single lumen; and a second plurality of side ports in the second section having less drainage activity than the first plurality of active side ports in the first section, each side port of the second plurality of side ports in communication with the single lumen;

wherein the active side ports in the first section provide increased drainage in the kidney-ureter junction region;

wherein at least one side port in the first section is configured to have more drainage activity than at least one other side port in the first section;

wherein each of the second plurality of side ports on the second section is offset rotated from about 30° to about 90° relative to each adjacent side port.

\* \* \* \* \*